US012616813B2

(12) United States Patent
Wiemker et al.

(10) Patent No.: US 12,616,813 B2
(45) Date of Patent: May 5, 2026

(54) PENDELLUFT DETECTION BY ACOUSTIC INTERFEROMETRY THROUGH AN ENDOTRACHEAL TUBE

(71) Applicant: KONINKLIJKE PHILIPS N.V., Eindhoven (NL)

(72) Inventors: Rafael Wiemker, Hamburg (DE); Joerg Sabczynski, Norderstedt (DE); Thomas Koehler, Hamburg (DE); Cornelis Petrus Hendriks, Eindhoven (NL); Roberto Buizza, Eindhoven (NL); Jaap Roger Haartsen, Eindhoven (NL); Michael Polkey, London (GB); Rita Priori, Eindhoven (NL); Nataly Wieberneit, Hamburg (DE); Stefan Winter, Aachen (DE); Kiran Hamilton J. Dellimore, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 833 days.

(21) Appl. No.: 17/897,595

(22) Filed: Aug. 29, 2022

(65) Prior Publication Data

US 2023/0094608 A1 Mar. 30, 2023

Related U.S. Application Data

(60) Provisional application No. 63/248,678, filed on Sep. 27, 2021.

(51) Int. Cl.
*A61M 16/00* (2006.01)

(52) U.S. Cl.
CPC ... *A61M 16/024* (2017.08); *A61M 2016/0027* (2013.01); *A61M 2016/003* (2013.01); *A61M 2230/432* (2013.01)

(58) Field of Classification Search
CPC ........ A61M 16/024; A61M 2016/0027; A61M 2016/003; A61M 2230/432;
(Continued)

(56) References Cited

U.S. PATENT DOCUMENTS 6,168,568 B1 * 1/2001 Gavriely ................ A61B 5/087
                                             600/529
10,226,225 B2 * 3/2019 Rodriguez-Villegas .....................
                                             A61B 5/113
(Continued)

OTHER PUBLICATIONS

International Search Report for PCT/EP2022/076143 filed Sep. 21, 2022.
(Continued)

*Primary Examiner* — Brandy S Lee
*Assistant Examiner* — Tina Zhang
(74) *Attorney, Agent, or Firm* — Daniel H. Brean

(57) ABSTRACT

A respiratory monitoring device includes an electronic controller configured to: analyze an audio signal triggered during inspiratory and expiratory phases of a patient receiving mechanical ventilation therapy from a mechanical ventilator, the audio signal being acoustically coupled into the airway of the patient, to determine resonant frequencies of the airway; determine a shift in the resonant frequencies between the inspiratory and expiratory phases to determine a presence of pendelluft inside of a lung of the patient; and output an indication of the presence of pendelluft.

16 Claims, 2 Drawing Sheets

(58) Field of Classification Search
CPC ............... A61M 16/042; A61M 16/04; A61M 2205/3375; A61M 2205/581; A61M 2205/583; A61B 5/087; A61B 7/003; A61B 5/085; A61B 5/0836; A61B 5/091; A61B 5/4836; A61B 5/7282; A61B 5/742; A61B 2562/0204; A61B 5/08; A61B 5/0803; A61B 5/0816
USPC .......................... 600/301, 529, 300, 538, 484
See application file for complete search history.

(56) References Cited

U.S. PATENT DOCUMENTS

| | | | |
|---|---|---|---|
| 2011/0265795 A1 | 11/2011 | Tagawa | |
| 2013/0178756 A1 | 7/2013 | Suzuki | |
| 2014/0171817 A1* | 6/2014 | Blanch | A61M 16/0051 |
| | | | 128/204.23 |
| 2014/0243697 A1* | 8/2014 | Endo | A61B 7/003 |
| | | | 600/529 |
| 2016/0278663 A1* | 9/2016 | Freeman | A61M 16/021 |
| 2017/0074857 A1* | 3/2017 | Dennis | A61B 5/4848 |
| 2019/0274919 A1* | 9/2019 | Lee | A61H 23/04 |
| 2021/0196149 A1 | 7/2021 | Artunduaga | |
| 2021/0316094 A1* | 10/2021 | Kimm | A61M 16/024 |

OTHER PUBLICATIONS

Rao, A. et al., "Acoustic Methods for Pulmonary Diagnosis". IEEE Review in Biomedical Engineering, vol. 12, (2019), pp. 221-239.

Enokidani, Y. et al."Effects of ventilatory settings on pendelluft phenomenon during mechanical ventilation." Resp. Care 2021;66(1):1-10.

Coppadoro, A. et al., "Occurrence of pendelluft under pressure support ventilation in patients who failed a spontaneous breathing trial: an observational study." Ann Intensive Care (2020) 10:39.

Sang, L. et al., "Qualitative and quantitative assessment of pendulluft: a simple method based on electrical impedance tomography." Ann Intensive Care (2020) 10:39.

Varberg, T.D. et al., "Determining the Speed of Sound and Heat Capacity Ratios of Gases by Acoustic Interferometry." Journal of Chemical Education 2017 94(12), 1995-1998.

Guido, M. et al., "Position emission tomography imagining of regional pulmonary perfusion and ventilation." Proc Am Thorac Soc. 2005;2(6):522-509.

* cited by examiner

PENDELLUFT DETECTION BY ACOUSTIC INTERFEROMETRY THROUGH AN ENDOTRACHEAL TUBE

CROSS-REFERENCE TO RELATED APPLICATIONS

This patent application claims the priority benefit under 35 U.S.C. § 119(e) of U.S. Provisional Application No. 63/248,678, filed on Sep. 27, 2021, the contents of which are herein incorporated by reference.

The following relates generally to the respiratory therapy arts, tracheal intubation arts, airway acoustic monitoring arts, pendelluft detection arts, and related arts.

BACKGROUND

Mechanical ventilation (MV) of a patient typically entails placement of an endotracheal tube (ETT) into a trachea of the patient, in a process known as tracheal intubation. The desired position of the tip of an ETT is approximately 5.0 cm (±2.0 cm) above a carina (i.e., a location where the trachea splits into the main right and left bronchus). Tracheal intubation is usually performed by an anesthesiologist or other qualified medical professional, and in a common sequence the head is moved backward to access the airway, and a laryngoscope is used to facilitate proper placement of the ETT between the vocal cords and into the trachea, without misplacement into the esophagus.

Common situations where mechanical ventilation is required can include intensive care unit (ICU) cases and during major surgery. Such patients often have images (e.g., computed tomography (CT) images) obtained of the thorax before being sent to the ICU, in particular if the patient's condition is a lung-related disease (e.g., Covid-19), or trauma.

An example of a condition that can lead to ventilation-induced lung injury (VILI) associated with assisted MV is the development of "pendelluft". Pendelluft is defined as oscillatory gas movement inside the lung, for example involving the displacement of gas from a more recruited non-dependent (ND) or "faster" lung region to a less recruited dependent (D) or "slower" lung region with minimal changes in the tidal volume (TV) of the ventilator (see, e.g., Enokidani et al. Effects of ventilatory settings on pendelluft phenomenon during mechanical ventilation. Resp Care 2021; 66(1):1-10). Pendelluft may cause lung over-stretching, tidal recruitment, and inflammation, due to over-inflation in the D lung region and collapse in the ND lung region. Since pendelluft develops without changes in VT of the ventilator, it is challenging for clinicians to recognize its presence via ordinary monitoring during MV. Early detection of pendelluft is important so that the treatment and/or ventilation strategies can be adjusted to ensure patient safety and better clinical outcomes.

However, there is currently no widely accepted standard test to confirm the presence of pendelluft. The most commonly reported diagnostic approach relies on electrical impedance tomography (EIT) (see, e.g., Coppadoro A. et al. Occurrence of pendelluft under pressure support ventilation in patients who failed a spontaneous breathing trial: an observational study. Ann Intensive Care (2020) 10:39; Sang L. et al. Qualitative and quantitative assessment of pendelluft: a simple method based on electrical impedance tomography. Ann Transl Med 2020; 8(19):1216), although other imaging techniques are sometimes used. Pathological alterations in lungs can be observed by computed tomography (CT), magnetic resonance imaging (MM), pulmonary ultrasound, and positron emission tomography (PET). CT and MRI can provide indirect information on regional time constants, while PET can be used to capture the clearance of the tracer nitrogen-13 which can be used to calculate the pendelluft (see, e.g., Musch G, Venegas JG. Positron emission tomography imaging of regional pulmonary perfusion and ventilation. *Proc Am Thorac Soc.* 2005; 2(6):522-509). However, with the exception of ultrasound these non-EIT based approaches are all unsuitable for real-time, semi-continuous, diagnosis of pendelluft at the bedside.

One example of an EIT-based approach for detecting pendelluft, described by Coppadoro et al., is to analyze global and regional EIT traces and ventilator waveforms, to determine if there is a phase-shift of the regional EIT signal compared to the global signal in two distinct time-periods: before and after the transition point from expiration to inspiration ($T_0$). Before $T_0$, the lung is still expiring and tracheal airflow is directed outward; regions of interest (ROIs) inflating during expiration must gain gas from other ROIs that are deflating, indicating the pendelluft phenomenon. Conversely, after $T_0$ tracheal airflow is directed inward, and gas lost by late-deflating ROIs must be gained from the other ROIs that are inflating, indicating the pendelluft phenomenon as well.

Although EIT-based approaches are often used to detect pendelluft, they still have some drawbacks and limitations. Many approaches rely on comparing impedance-time curves from different ROIs, which is time-consuming and may miss the pendelluft depending on the division of ROIs. Another drawback is that many EIT-based techniques require an interruption of normal ventilation or only provide a qualitative measurement, which may be insufficient to guide clinical decision making. Yet another drawback is the need for mounting further instrumentation and sensors onto the patient.

The following discloses certain improvements to overcome these problems and others.

SUMMARY

In one aspect, a respiratory monitoring device includes an electronic controller configured to: analyze an audio signal triggered during inspiratory and expiratory phases of a patient receiving mechanical ventilation therapy from a mechanical ventilator, the audio signal being acoustically coupled into the airway of the patient, to determine resonant frequencies of the airway; determine a shift in the resonant frequencies between the inspiratory and expiratory phases to determine a presence of pendelluft inside of a lung of the patient; and output an indication of the presence of pendelluft.

In another aspect, a respiratory monitoring method includes, with an electronic controller, analyzing an audio signal triggered during inspiratory and expiratory phases of a patient receiving mechanical ventilation therapy from a mechanical ventilator, the audio signal being acoustically coupled into the airway of the patient, to determine resonant frequencies of the airway; determining a shift in the resonant frequencies between the inspiratory and expiratory phases to determine a presence of pendelluft inside of a lung of the patient; and outputting an indication of the presence of pendelluft.

One advantage resides in detecting a presence of pendelluft in a patient undergoing MV therapy.

Another advantage resides in detecting a presence of pendelluft in a patient undergoing MV therapy without altering an ETT inserted into the patient during MV therapy.

Another advantage resides in detecting a presence of pendelluft in a patient undergoing MV therapy without attaching additional devices to the patient.

Another advantage resides in detecting a presence of pendelluft in a patient undergoing MV therapy by displaying an indication of pendelluft either on a smart device or on a display of a mechanical ventilator, allowing a low-cost and portable solution also suitable for out-of-hospital situations. Optionally, the indication of pendelluft can be presented as a notification pushed by an associated application program ("app") running on the smart phone, and/or as an alert issued by the controller of the mechanical ventilator or other patient monitoring equipment.

Another advantage resides in detecting a presence of pendelluft in a patient undergoing MV therapy with an audio sensor attached to an ETT inserted into a trachea of the patient, in which the audio sensors can be disposable to comply with hygienic standards.

Another advantage resides in detecting a presence of pendelluft in a patient undergoing MV therapy with less technical skill than performing an imaging examination to detect a presence of pendelluft.

Another advantage resides in detecting a presence of pendelluft in a patient undergoing MV therapy without having to expose the patient to ionizing radiation.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
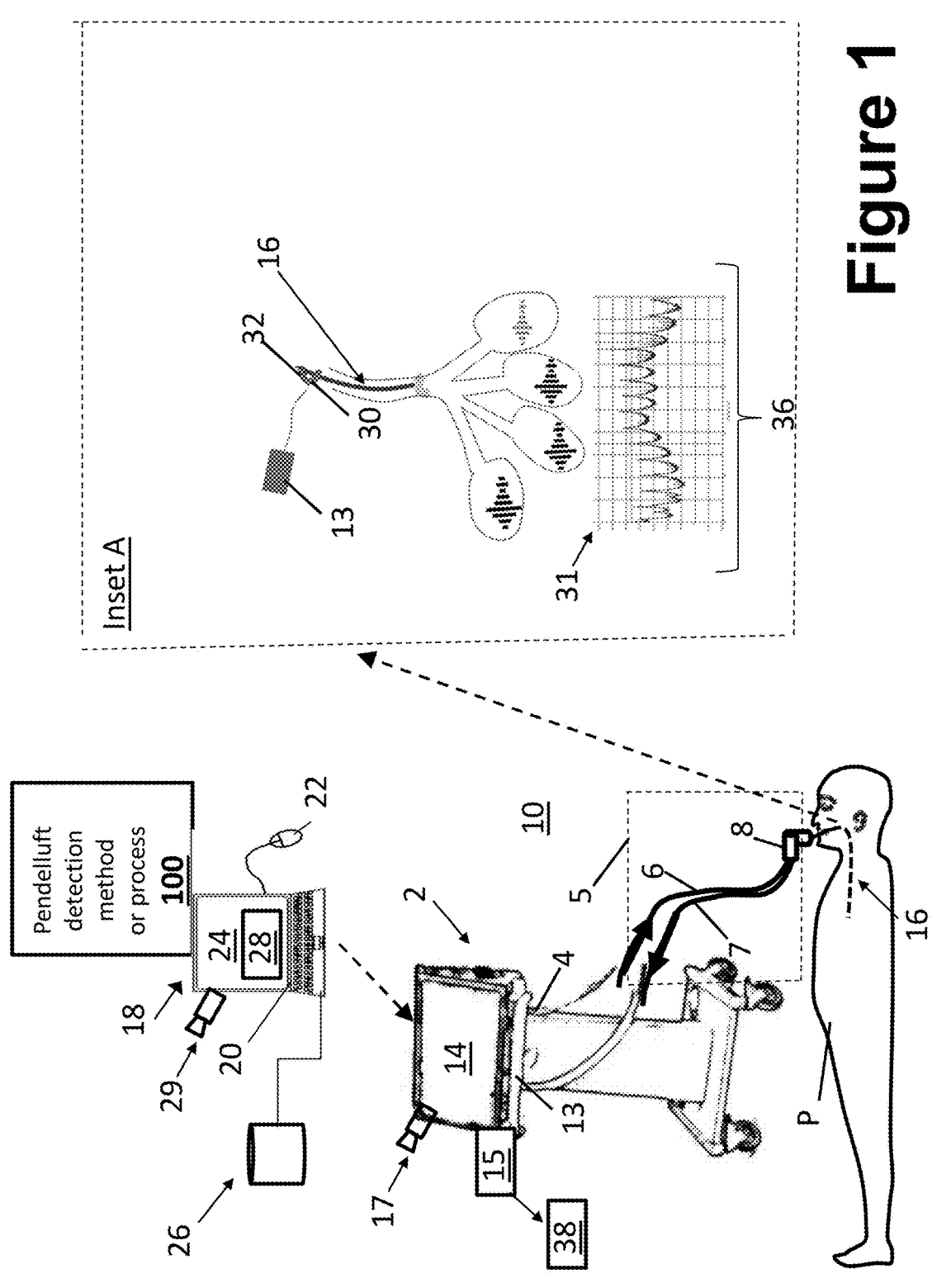
FIG. 1 diagrammatically shows an illustrative mechanical ventilation system in accordance with the present disclosure.

As used herein, the singular form of "a", "an", and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one and the same item of hardware.

With reference to FIG. 1, a mechanical ventilator 2 for providing ventilation therapy to an associated patient P is shown. As shown in FIG. 1, the mechanical ventilator 2 includes an outlet 4 connectable with a patient breathing circuit 5 to deliver mechanical ventilation to the patient P. The patient breathing circuit 5 includes typical components for a mechanical ventilator, such as an inlet line 6, an optional outlet line 7 (this may be omitted if the ventilator employs a single-limb patient circuit), a connector or port 8 for connecting with an ETT, and one or more breathing sensors (not shown), such as a gas flow meter, a pressure sensor, end-tidal carbon dioxide ($etCO_2$) sensor, and/or so forth. The mechanical ventilator 2 is designed to deliver air, an air-oxygen mixture, or other breathable gas (supply not shown) to the outlet 4 at a programmed pressure and/or flow rate to ventilate the patient via an ETT. The mechanical ventilator 2 also includes a controller 13 (e.g., an electronic processor or a microprocessor), a display device 14 (e.g., an LCD display, plasma display, cathode ray tube display, and/or so forth), and a non-transitory computer readable medium 15 storing instructions executable by the controller 13. The non-transitory computer readable medium 15 may, by way of nonlimiting illustrative example, include one or more of a magnetic disk, RAID, or other magnetic storage medium; a solid-state drive, flash drive, electronically erasable read-only memory (EEROM) or other electronic memory; an optical disk or other optical storage; various combinations thereof; or so forth; and may be for example a network storage, an internal hard drive, various combinations thereof, or so forth.

FIG. 1 diagrammatically illustrates the patient P intubated with an endotracheal tube (ETT) 16 (the lower portion of which is inside the patient P and hence is shown in phantom). The connector or port 8 connects with the ETT 16 to operatively connect the mechanical ventilator 2 to deliver breathable air to the patient P via the ETT 16. The mechanical ventilation provided by the mechanical ventilator 2 via the ETT 16 may be therapeutic for a wide range of conditions, such as various types of pulmonary conditions like emphysema or pneumonia, viral or bacterial infections impacting respiration such as a COVID-19 infection or severe influenza, cardiovascular conditions in which the patient P receives breathable gas enriched with oxygen, or so forth.

FIG. 1 shows the patient P already intubated. That is, FIG. 1 shows the patient after a tracheal intubation has been performed to insert the ETT 16 into the patient. However, to safely perform the tracheal intubation, the anesthesiologist or other qualified medical professional first performs an assessment of the patient P to select the ETT size of the ETT 16, and then inserts an ETT of the selected size into the patient P by a tracheal intubation procedure.

With continuing reference to FIG. 1, a pendelluft monitoring device 18 can be included, and configured to assist with detecting a presence of pendelluft in the patient P. The pendelluft monitoring device 18 can comprise an electronic processing device, such as a workstation computer (more generally, a computer), a smart device (e.g., a smartphone, a tablet, and so forth), or server computer or a plurality of server computers, (e.g., interconnected to form a server cluster, cloud computing resource, or so forth). In some embodiments, the pendelluft monitoring device may be integral with the controller 13 of the mechanical ventilator 2, for example comprising additional programming of the controller 13. In some embodiments, the pendelluft monitoring device may be integral with a multifunction bedside patient monitor, for example comprising additional programming of the patient monitor. The pendelluft monitoring device 18 includes typical components, such as an electronic controller 20 (e.g., an electronic processor or a micropro-cessor), optionally at least one user input device (e.g., a mouse, a keyboard, a trackball, a finger swipe on a touch-screen of a smart device, and/or the like) 22, and at least one display device 24 (e.g., an LCD display, plasma display, cathode ray tube display, and/or so forth) and/or other output device. In some embodiments, the display device 24 can be a separate component from the electronic processing device 18. The display device 24 may also comprise two or more display devices.

The electronic controller 20 is operatively connected with one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the pendelluft monitoring device 18, various combinations thereof, or so forth. It is to be understood that any reference to a non-transitory medium or media 26 herein is to be broadly construed as encompassing a single medium or multiple media of the same or different types. Likewise, the electronic controller 20 may be embodied as a single electronic processor or as two or more electronic processors. The non-transitory storage media 26 stores instructions executable by the at least one electronic controller 20. The instructions include instructions to generate a graphical user interface (GUI) 28 for display on the remote operator display device 24. The electronic processing device 18 also includes a loudspeaker 29 for outputting audio signals.

As shown in inset A of FIG. 1, an audio transducer 30 attached to a portion of the ETT 16 that is not disposed in the trachea of the patient P. The audio transducer 30 is configured to generate an audio signal 31 acoustically coupled with the ETT 16 that is triggered during inspiratory and expiratory phases of the patient P receiving MV therapy from the mechanical ventilator 2. In some examples, the audio transducer 30 comprises a speaker 30. In addition, a microphone 32 is also acoustically coupled with the ETT 16 and configured to receive the audio signal 31. For example, the speaker 30 and the microphone 32 can be clipped on to the ETT 16, and in electronic communication (e.g., by a wired connection, or by a wireless connection such as a Bluetooth™ connection) with the electronic controller 13 of the mechanical ventilator 2 and/or the electronic controller 20 of the electronic processing device 18. (Note, Inset A diagrammatically indicates the electronic controller 13). If various local parts of the lung move in a contra-phasic movement, then the difference (shift) in resonant frequency spectrum is diminishing. Inset A also shows the audio signal 31, and schematically shows resonant frequencies 36 within different portions of the lung of the patient P.

Furthermore, as disclosed herein, the non-transitory com-puter readable medium 15 of the mechanical ventilator 2 and/or the non-transitory storage media 26 of the electronic processing device 18 stores instructions executable by the at least one electronic controller 20 to perform a pendelluft detection method or process 100.

Figure 2:
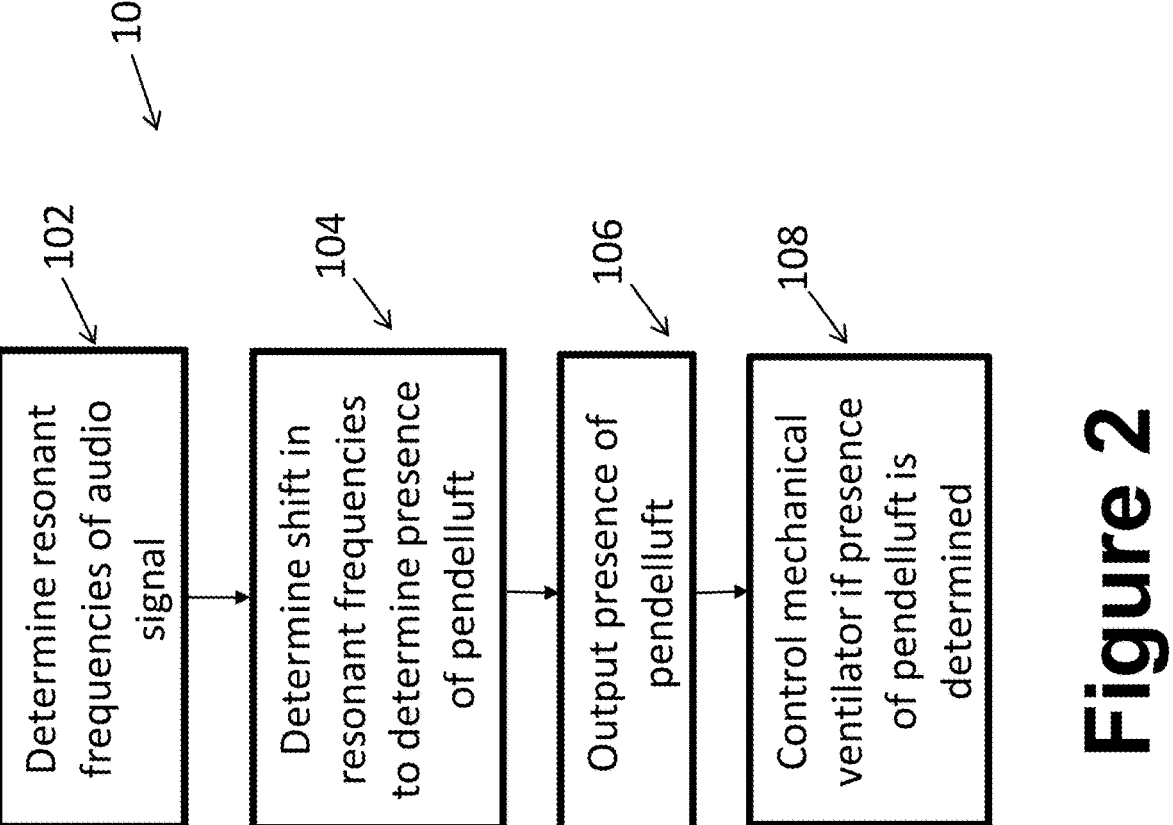
FIG. 2 shows an example flow chart of operations suitably performed by the system of FIG. 1.

With reference to FIG. 2, and with continuing reference to FIG. 1, an illustrative embodiment of the pendelluft detec-tion method 100 is diagrammatically shown as a flowchart. As described herein, the method 100 is performed by the electronic controller 13 of the mechanical ventilator 2. However, the method 100 can suitably be performed by the electronic controller 20 of the electronic processing device

18. For example, if a visual message generated during the method 100 can be displayed on the display device 14 of the mechanical ventilator 2, then the same message can be suitably displayed on the display device 24 of the electronic processing device 18. These are merely examples.

To begin the method 100, the ETT 16 can be inserted into the trachea of the patient P, and the speaker 30 and the microphone 32 can be clipped to the portion of the ETT 16 that is not inserted into the trachea of the patient P. At an operation 102, the audio signal 31 is analyzed to determine resonant frequencies 36 of the airway of the patient P. The audio signal 31 is acoustically coupled with the ETT 16 that is triggered during inspiratory and expiratory phases of the patient P receiving MV therapy from the mechanical venti-lator 2. The audio signal 31 can be, for example, a chirp signal, and the resonant frequencies 36, for example, can be in a range of 100 Hz-5 kHz. In another example, the audio signal 31 comprises a chirp impulse as the audio signal 31, and an impulse responses comprises the resonant frequen-cies 36.

At an operation 104, a shift in the resonant frequencies 36 between the inspiratory and expiratory phases is determined in order to determine a presence of pendelluft indicative of oscillatory gas movement inside of a lung of the patient P. The resonant frequencies 36 can exhibit a change between the inspiratory and expiratory phases because of (i) opposing movement of the air as a medium carrying the audio signal 31, and dilation and extension of the bronchi of the patient P (see, e.g., Thomas D. Varberg, Bradley W. Pearlman, Ian A. Wyse, Samuel P. Gleason, Dalir H. P. Kellett, and Kenneth L. Moffett, Determining the Speed of Sound and Heat Capacity Ratios of Gases by Acoustic Interferometry, Journal of Chemical Education 2017 94 (12), 1995-1998). A presence of pendelluft diminishes the shift (i.e., a difference) of resonant frequencies 36 between inspiratory and expira-tory phases, as local parts of the gas stream are inverted, and opposing local signals are superimposed. In one example, the shift determination operation 104 includes measuring a cross-correlation or a cross-entropy of the resonant frequen-cies 36 between the inspiratory and expiratory phases. In another example, the shift determination operation 104 includes implementing a trained artificial neural network (ANN) 38 into the electronic controller 13 of the mechanical ventilator 2 (or the electronic controller 20 of the electronic processing device 18) to detect and quantify the presence of pendelluft. For example, training data for training the ANN can be acquired of reference patients monitored by the audio transducer 30 and microphone 32 to determine any shift in the resonant frequencies, and also connected with electrical impedance tomography (EIT) for providing ground truth information on if/when pendelluft occurs.

In some embodiments, feedback on whether pendelluft oscillations occur can be provided to the user (e.g., with a visual signal output via the display device 14 or an audio signal output the loudspeaker 17).

At an operation 106, an indication of the presence of pendelluft is output, for example on the display device 14 or the loudspeaker 17. Since pendelluft can be an early indi-cation of increased likelihood of ventilation-induced lung injury (VILI), or even an indication of incipient VILI, the operation 106 may optionally provide an alert or urgent notification to a nurse, pulmonologist, or other medical professional. For example, the operation 106 may include presenting an indication of pendelluft as a notification pushed by an associated application program ("app") run-ning on a smart phone carried by the nurse, pulmonologist, or so forth, and/or may be issued as an alert issued by the controller of the mechanical ventilator or other patient monitoring equipment, and/or an alert at a nurses' station. At an optional operation 108, the electronic controller 13 can control the mechanical ventilator 2 adjust one or more parameters of the mechanical ventilation therapy delivered to the patient in response to the indication of the presence of pendelluft.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A respiratory monitoring device comprising an electronic controller configured to:
    analyze an audio signal triggered during inspiratory and expiratory phases of a patient receiving mechanical ventilation therapy from a mechanical ventilator, the audio signal being acoustically coupled into the airway of the patient, to determine resonant frequencies of the airway;
    determine a shift between a resonant frequency at the inspiratory phase and a resonant frequency at the expiratory phase; and
    if there is a diminishment of the shift between the resonant frequency at the inspiratory phase and the resonant frequency at the expiratory phase, output an indication of the presence of pendelluft inside a lung of the patient.

2. The device of claim 1, wherein the electronic controller is configured to determine the shift in the resonant frequencies between the inspiratory and expiratory phases by:
    measuring a cross-correlation or a cross-entropy of the resonant frequencies between the inspiratory and expiratory phases.

3. The device of claim 1, wherein the electronic controller is configured to determine the shift in the resonant frequencies between the inspiratory and expiratory phases by:
    implementing a trained artificial neural network (ANN) to detect and quantify the presence of pendelluft.

4. The device of claim 1, wherein the electronic controller is further configured to:
    provide feedback to a user to validate a setup of the mechanical ventilator when a result of analyzing the audio signal is ambiguous or atypical.

5. The device of claim 1, further comprising a display device, wherein the electronic controller is configured to output the indication of the presence of pendelluft by:
    displaying the indication of the presence of pendelluft on the display device.

6. The device of claim 1, further comprising a loudspeaker, wherein the electronic controller is configured to:
    output the indication of the presence of pendelluft via the loudspeaker.

7. The device of claim 1, wherein the mechanical ventilation therapy is delivered by an endotracheal tube (ETT), and the device further includes:
    an audio transducer attached to a portion of the ETT not disposed within the trachea, the audio transducer configured to generate the audio signal acoustically coupled with the ETT.

8. The device of claim 7, further including:
    a microphone acoustically coupled with the ETT and configured to receive the audio signal.

9. The device of claim 1, wherein the electronic controller is configured to analyze the audio signal to determine the resonant frequencies of the audio signal in a range of 100 Hz-5 kHz.

10. The device of claim 1, wherein the audio signal comprises a chirp signal.

11. A respiratory therapy device, comprising:
    a mechanical ventilator configured to deliver mechanical ventilation therapy to a patient; and
    a respiratory monitoring device as set forth in claim 1.

12. The respiratory therapy device of claim 11, wherein the at least one electronic controller of the respiratory monitoring device is further configured to:
    control the mechanical ventilator to adjust one or more parameters of the mechanical ventilation therapy delivered to the patient in response to the indication of the presence of pendelluft.

13. A respiratory monitoring method, comprising, with an electronic controller:
    analyzing an audio signal triggered during inspiratory and expiratory phases of a patient receiving mechanical ventilation therapy from a mechanical ventilator, the audio signal being acoustically coupled into the airway of the patient, to determine resonant frequencies of the airway;
    determining a shift between a resonant frequency at the inspiratory phase and a resonant frequency at the expiratory phase; and
    if there is a diminishment of the shift between the resonant frequency at the inspiratory phase and the resonant frequency at the expiratory phase, outputting an indication of the presence of pendelluft inside of a lung of the patient.

14. The method of claim 13, wherein determining the shift in the resonant frequencies between the inspiratory and expiratory phases includes:
    measuring a cross-correlation or a cross-entropy of the resonant frequencies between the inspiratory and expiratory phases.

15. The method of claim 13, wherein determining the shift in the resonant frequencies between the inspiratory and expiratory phases includes:
    implementing a trained artificial neural network (ANN) to detect and quantify the presence of pendelluft.

16. A respiratory monitoring device comprising an electronic controller configured to:
    analyze an audio signal triggered during inspiratory and expiratory phases of a patient receiving mechanical ventilation therapy from a mechanical ventilator, the audio signal being acoustically coupled into the airway of the patient, to determine resonant frequencies of the airway;
    determine a shift between a resonant frequency at the inspiratory phase and a resonant frequency at the expiratory phase;
    detect a presence of pendelluft inside of a lung of the patient as a diminishment of the shift between the resonant frequency at the inspiratory phase and the resonant frequency at the expiratory phase; and
    output an indication of the presence of pendelluft.

* * * * *